United States Patent
Noordam

(10) Patent No.: US 9,192,184 B2
(45) Date of Patent: Nov. 24, 2015

(54) PROCESS FOR THE PRODUCTION OF YEAST EXTRACTS HAVING LOW TURBIDITY

(75) Inventor: Bertus Noordam, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 36 days.

(21) Appl. No.: 13/984,755

(22) PCT Filed: Feb. 15, 2012

(86) PCT No.: PCT/EP2012/052546
§ 371 (c)(1),
(2), (4) Date: Aug. 9, 2013

(87) PCT Pub. No.: WO2012/110534
PCT Pub. Date: Aug. 23, 2012

(65) Prior Publication Data
US 2013/0316047 A1    Nov. 28, 2013

Related U.S. Application Data

(60) Provisional application No. 61/443,892, filed on Feb. 17, 2011.

(30) Foreign Application Priority Data

Feb. 17, 2011    (EP) .................................... 11154879

(51) Int. Cl.
*A23L 1/28*    (2006.01)
*A23L 1/30*    (2006.01)
*C12N 1/06*    (2006.01)
*C12N 1/16*    (2006.01)

(52) U.S. Cl.
CPC ................. *A23L 1/28* (2013.01); *A23L 1/3018* (2013.01); *C12N 1/063* (2013.01); *C12N 1/16* (2013.01); *A23V 2002/00* (2013.01)

(58) Field of Classification Search
CPC ..... A23L 1/28; A23L 1/3018; A23V 2002/00
USPC .................................................... 426/60, 655
See application file for complete search history.

(56) References Cited

U.S. PATENT DOCUMENTS

| | | |
|---|---|---|
| 4,303,680 A | 12/1981 | Tanekawa et al. |
| 5,188,852 A | 2/1993 | Origane et al. |
| 2006/0140974 A1 | 6/2006 | Choe et al. |

FOREIGN PATENT DOCUMENTS

| | | | | |
|---|---|---|---|---|
| GB | 1071027 A | 6/1967 | | |
| JP | 2006296407 A | * 11/2006 | ............... | C12G 3/00 |

OTHER PUBLICATIONS

JP-2006-296407A—Machine Translation.*
Champagne, C. P. 1999. Food Res. International. 32: 575-583.*
Breddman, K. et al. 1991. Appl. Microbiol. Biotechnol. 35: 423-329.*
International Search Report for PCT/EP2012/052546 Mailed June 19, 2012.

* cited by examiner

*Primary Examiner* — Hamid R Badr
(74) *Attorney, Agent, or Firm* — Miles and Stockbridge

(57) ABSTRACT

A process to produce a yeast extract is described comprising a) subjecting yeast to autolysis; and b) subjecting the autolysate to solid/liquid separation and recovering the soluble fraction, whereby the solid/liquid separation in step b) is done at a pH of less than 5.1. The process of the invention is simple, has a high yield, and results in a yeast extract having low turbidity.

8 Claims, No Drawings

PROCESS FOR THE PRODUCTION OF YEAST EXTRACTS HAVING LOW TURBIDITY

CROSS REFERENCE TO RELATED APPLICATIONS

This application is a §371 National Stage Application of PCT/EP2012/052546, filed Feb. 15, 2012, which claims priority to European Application No. 11154879.8, filed Feb. 17, 2011, and to U.S. Provisional Application No. 61/443,892 filed Feb. 17, 2011.

BACKGROUND

1. Field of the Invention

The present invention relates to a process for the production of yeast extracts.

2. Description Of Related Art

Yeast extracts are commonly used in the food industry to improve or enhance the flavour of all sorts of savoury food applications such as in soups, crisps, chips, (processed) meats, etceteras.

The Food Chemical Codex defines a "yeast extract" as follows: "Yeast Extract comprises the water soluble components of the yeast cell, the composition of which is primarily amino-acids, peptides, carbohydrates and salts. Yeast extract is produced through the hydrolysis of peptide bonds by the naturally occurring enzymes present in edible yeast or by the addition of food-grade enzymes". In contrast, the same Food Chemical Codex defines "autolysed yeast" as "the concentrated, nonextracted, partially soluble digest obtained from food-grade yeast. Solubilization is accomplished by enzyme hydrolysis or autolysis of yeast cells. Food-grade salts and enzymes may be added. Yeast, autolyzed, contains both soluble and insoluble components derived from the whole yeast cell. It is composed primarily of amino acids, peptides, carbohydrates, fats, and salts". A yeast autolysate therefore differs from a "yeast extract" because the yeast autolysate, in addition to all the interesting components present in yeast extracts, also contains interesting cell wall components which are not separated from the soluble fraction.

Yeast extracts are generally produced by:
a) subjecting a yeast to autolysis; and
b) subjecting the autolysate to solid/liquid separation and recovering the liquid fraction.

Usually such a process starts with a cream yeast which is obtained by removing the waste liquor after harvesting of the yeast cells at the end of a fermentation, i.e. by removing the vinasse. Next, the yeast cells in the cream yeast are treated such that the cells are disrupted and contents are released. This is generally done by two different processes, resulting in either autolytic yeast extracts or hydrolytic yeast extracts.

Autolytic yeast extracts are concentrates of the soluble materials obtained from yeast after disruption of the cells and digestion (lysis) of the polymeric yeast material. The active yeast enzymes released in the medium after cell disruption are responsible for the lysis. Generally these types of yeast extracts do not comprise 5'-ribonucleotides because during the autolytic process the native RNA is decomposed or modified in a form which is not or almost not degradable into 5'-ribonucleotides. These types of yeast extract, which are rich in amino acids, are used in the food industry as basic taste providers. The amino acids present in the yeast extract add a bouillon-like, brothy taste to the food.

Hydrolytic yeast extracts, on the other hand, are concentrates of the soluble materials obtained from yeast after disruption of the cells, digestion (lysis) and addition of proteases and/or peptidases and especially nucleases to the yeast suspension during lysis. The native yeast enzymes are inactivated prior to the lysis, generally by a heat shock.

A problem with yeast extracts obtained by processes known in the art is that they may be turbid when dissolved, which can be a disadvantage in clear applications such as clear soups and the like. A possible solution for this turbidity is to apply extra filtration steps such as ultrafiltration or microfiltration. However, not only is this not economical since it requires additional process steps, but it also leads to losses since the material which causes the turbidity stays behind the filter and is discarded.

SUMMARY

It is an object to provide a process to produce yeast extracts low in turbidity which is simple and has a high yield based on dry matter.

In a first aspect the present invention provides a process to produce a yeast extract comprising:
a) subjecting a yeast to autolysis; and
b) subjecting the autolysate to solid/liquid separation and recovering the soluble fraction, whereby the solid/liquid separation in step b) is done at a pH of lower than 5.1 and higher than 1.0.

DETAILED DESCRIPTION OF A PREFERRED EMBODIMENT

In the context of the invention, the "recovered soluble fraction" obtained in step b) is a yeast extract. Therefore, throughout this specification the term "recovered soluble fraction obtained in step b)" has the same meaning as "yeast extract obtained in step b)".

In the context of the present invention "autolysis" of a yeast is defined as a process wherein degradation of the yeast cells and of the polymeric yeast material is at least partially effected by active native yeast enzymes released in the medium after (partially) damaging and/or disrupting the yeast cell wall.

Examples of preferred yeast are *Saccharomyces*, *Kluyveromyces* and *Candida*. Strains belonging to the genus *Saccharomyces*, in particular belonging to the species *Saccharomyces cerevisiae* are most preferred.

The yeast used in the process of the invention may be prepared by any suitable fermentation process known in the art. The yeast biomass may be concentrated prior to its use in the present process, for example by centrifugation or filtration. For example, cream yeast (baker's yeast which has been concentrated to a dry matter content of 15-27% w/w) may be used. Optionally fermentation broths comprising Brewer's yeast or residue yeast derived from breweries (spent Brewer's yeast) may be used.

The present invention provides a process which is especially suitable for large scale production of yeast extracts. Large scale means that fermentation is performed in fermentors of more than 10 m$^3$.

The autolytic process is initiated by damaging and/or partially disrupting the yeast cell walls. This way the cells are partially opened and at least some of the cell content is released. In order to damage and/or partially disrupt the yeast cell walls, the cells are treated chemically, mechanically or enzymatically using methods known to those skilled in the art.

Mechanical treatments include homogenisation techniques. At this purpose, use of high-pressure homogenisers is possible. Other homogenisation techniques may include mixing with particles, e.g. sand and/or glass beads, or the use of a milling apparatus (e.g. a bead mill).

Chemical treatments include the use of salts, alkali and/or one or more surfactants or detergents. Chemical treatments are less preferred because they may lead to partial degradation of RNA especially when alkali is used, with consequent formation of 2'-ribonucleotides and 3'-ribonucleotides.

The inventors have realized that a yeast extract having very low turbidity (i.e. a very clear yeast extract) may be produced when the pH during the recovering in step b) is lower than 5.1 and higher than 1.0.

"Turbidity", also referred to as "cloudiness" or "haziness", is typically caused by suspended particles in a liquid. The skilled person knows how to measure turbidity. A suitable method to measure turbidity is described in Example 1. Throughout this specification the terms "a clear yeast extract" and "a yeast extract having low turbidity" are understood to have the same meaning.

In an embodiment, the pH during the solid/liquid separation in step b) is lower than 5.1, preferably 4.5 or less, more preferably 4.2 or less, even more preferably 4.0 or less, most preferably 3.5 or less1 and higher than 1.0. Preferred pH-ranges are from 1.0-5.0 or from 1.0-4.5 or from 1.0-4.2 or from 1.0-3.5 and from 2.0-5.1 or from 2.0-4.5 or from 2.0-4.2. Most preferred is the pH range 2.0-3.5.

The solid-liquid separation in step b) is preferably done by common solid-liquid separation methods, preferably by centrifugation or filtration. When centrifugation is used, the soluble fraction can be recovered as the supernatant.

In a preferred embodiment the solid-liquid separation in step b) is done by centrifugation. Use of centrifugation is economically advantageous, in particular when the process is performed at large scale.

In the process of the invention the conditions used in the autolytic process are preferably such that a substantial part of the RNA remains in a form degradable into 5'-ribonucleotides.

With the term "5'-ribonucleotides" it is herewith intended a mixture of 5'-GMP, 5'-CMP, 5'-UMP and further 5'-AMP and/or 5'-IMP, wherein said 5'-AMP may be either partially or completely converted into 5'-IMP. The term "5'-ribonucleotide(s)" encompasses the free 5'-ribonucleotide as well as a salt thereof.

In this context, with "substantial part of the RNA" is meant preferably at least 50%, more preferably at least 60%, 70%, 75%, even more preferably at least 80%, most preferably at least 83%, al based on the total amount of RNA prior to step b). A high amount of RNA which is degradable into 5'-ribonucleotides may advantageously result in a yeast extract having a very low turbidity. The RNA does not need to remain fully intact during the autolytic process, but at least a substantial part of the RNA should remain in a form degradable into 5'-ribonucleotides. Generally up to 100% of the RNA may remain in a form degradable into 5'-ribonucleotides. "In a form degradable into 5'-ribonucleotides" means that the RNA should be in a form that allows conversion into 5'-ribonucleotides by a suitable enzyme. Preferably the suitable enzyme is a 5'-phosphodiesterase (5'-Fdase).

A form of RNA degradable into 5'-ribonucleotides comprises oligonucleotides containing at least two ribonucleotide units. Therefore RNA in a form degradable into 5'-ribonucleotides may consist of a mixture comprising intact RNA and oligonucleotides or polynucleotides of different lengths. In the context of the present invention an oligonucleotide comprises 2-10 ribonucleotide units, while a polynucleotide comprises more than 10 ribonucleotide units.

The percentage of RNA which remains in a form degradable into 5'-ribonucleotides during the autolytic process is defined as the ratio (x 100) between a) the weight percentage of 5'-GMP (calculated as the disodium heptahydrate thereof and based on sodium chloride free dry matter) measured in the autolysate after inactivation of the enzymes participating in the autolysis and conversion of RNA into 5'-ribonucleotides, and b) the weight percentage of GMP (calculated as the disodium heptahydrate thereof and based on sodium chloride free dry matter) measured in the starting material after complete alkaline hydrolysis of RNA. The weight percentage of GMP (calculated as the disodium heptahydrate thereof and based on sodium chloride free dry matter) measured in the starting material after alkaline hydrolysis can be determined from the corresponding weight percentage of free GMP (based on sodium chloride free dry matter) by multiplying the latter with a factor 1.47. The method to determine the amount of 5'-GMP in the autolysate and of GMP after basic hydrolysis is described in Example 1. The method used to determine the amount of 5'-GMP can also be used to determine the amount of 5'-IMP, 5'-AMP, 5'-CMP and 5'-UMP if necessary with some modifications well within the knowledge of those skilled in the art.

Preferably damaging and/or partially disrupting the yeast cell wall is done enzymatically because a better control of the process can thereby be achieved and because this method is especially suitable to be used at large scale. Several enzyme preparations can be used like cellulases, glucanases, hemicellulases, chitinases, proteases and/or pectinases. Preferably protease is used, more preferably endoprotease is used. The conditions used to initiate the autolytic process are dependent on the type of enzyme used and can be easily determined by those skilled in the art. Generally the conditions used to enzymatically damage and/or disrupt the yeast cell wall will correspond to those applied during the autolysis of the yeast.

The autolysis of the yeast is at least partially effected by active native yeast enzymes released in solution after (partially) damaging and/or disrupting the yeast cell wall wherein the chemicals, or more preferably, the enzymes added to damage and/or to disrupt the yeast cell wall may contribute to the degradation of the yeast cells and of polymeric yeast material.

In particular the first phase of autolysis is performed at a particular pH range combined with a particular temperature.

For instance, the conditions applied in the autolysis of *Saccharomyces cerevisiae* to ensure that a substantial part of the RNA remains in a form degradable into 5'-ribonucleotides and/or to decrease the turbidity of the recovered soluble fraction in step b) are such that the pH in the first phase of the autolysis is between 4.5-9 and/or the temperature is between 50-65° C. Preferably the first 8 hours of the autolysis, more preferably the first 4 hours of the autolysis, are performed at a pH of 4.5-5.5 and at a temperature of 57-65° C., or at a pH 5.5-9 and a temperature of 50-65° C.

The autolysis conditions to be kept after the first phase are less critical. After the first phase the pH is generally kept between 4 and 10 and the temperature is generally kept between 40° C. and 70° C. However, preferably the pH after the first phase is less than 5.1, preferably the pH after the first phase is 4.5 or less, more preferably 4.2 or less, even more preferably 4.0 or less, most preferably 3.5 or less. In general the duration of the autolytic process including the first phase is at most 24 hours.

The present invention may encompass as well a process wherein in step a) a yeast is subjected to hydrolysis under conditions at which a substantial part of the RNA remains in a form degradable into 5'-ribonucleotides. In the context of the present invention "hydrolysis of a yeast" is defined as a process wherein the native yeast enzymes have been inactivated and wherein suitable exogenous enzymes added to the yeast biomass to effect degradation of the yeast cells and of the polymeric yeast material.

After autolysis a suspension (autolysate) is obtained which comprises a yeast cell wall fraction, RNA which may be for a substantial part in a form degradable into 5'-ribonucleotides, and soluble cell components (e.g. proteins, peptides, amino acids, carbohydrates, etceteras). The cell wall fraction comprises insoluble cell residues, in particular cell walls or fragments thereof.

At the end of the autolytic process and prior to step b), the chemicals used for damaging and/or partially disrupting the yeast cell walls and/or the enzymes which took part in the autolytic process should preferably be neutralised and/or inactivated. The enzymes which took part in the autolysis are the native yeast enzymes and optionally any added exogenous enzyme used to initiate the autolytic process. Neutralisation and/or inactivation of the chemicals and/or the enzymes should occur under conditions at which a substantial part of the RNA remains in a form degradable into 5'-ribonucleotides. Inactivation of the enzymes which took part in the autolysis can be done by pH treatment or preferably by a heat treatment whereby the enzymes are inactivated. The enzymes can be inactivated by heat treatment, for instance by heating the mixture from 5 minutes to 1 hour at a temperature from 65° C. to 95° C., more preferably by heating from 30 minutes to 1 hour at a temperature from 65° C. to 75° C., wherein typically a shorter reaction time may be used at higher reaction temperatures. For example, heating the mixture for 1 hour at 65° C. or for 30 minutes at 75° C. may be sufficient to inactivate the enzymes.

In step b) of the process of the invention the autolysate is subjected to solid/liquid separation and the RNA-containing cell wall fraction is recovered, wherein the pH during this is lower than 5.1, preferably 4.5 or less, more preferably 4.2 or less, even more preferably 4.0 or less, most preferably 3.5 or less1 and higher than 1.0. Preferred pH-ranges are from 1.0-5.0 or from 1.0-4.5 or from 1.0-4.2 or from 1.0-3.5 and from 2.0-5.1 or from 2.0-4.5 or from 2.0-4.2. Most preferred is the pH range 2.0-3.5. In this solid/liquid separation the solid fraction, which consists mainly of cell walls, is separated from the soluble fraction.

In an embodiment, in step b) at least 55%, more preferably at least 75%, most preferably at least 90% of the total RNA remains associated with the cell wall fraction. Example 2 demonstrates that up to 94.7% of the total RNA in the autolysate remains associated with the cell wall fraction. It is also demonstrated in Example 2 that the percentage RNA bound to the yeast cell walls and the turbidity of the yeast extract are a function of the pH during the solid/liquid separation: at lower pH values, more RNA remains bound to the cell walls and the turbidity of the yeast extract is decreasing.

The total amount of RNA (i.e. prior to step b) can be determined by analyzing the autolysate obtained in step a). A method to analyze RNA is described in Example 1.

A high amount of RNA associated with the cell wall fraction may result in a yeast extract having low turbidity.

The percentage of the RNA which remains associated with the cell wall fraction is defined as the ratio (×100) between a) the amount of RNA in grams in the cell wall fraction of an autolysate originating from a fixed amount of starting material, and b) the amount of RNA in grams present in the same fixed amount of starting material. The method to determine the amount of RNA in the cell wall fraction and in the starting material is described in example 1.

In order to decrease the turbidity of the recovered soluble fraction in step b), the autolysate may be subjected to ultra filtration (UF) instead of to a common solid-liquid separation method like centrifugation or filtration. In general a larger molecular weight cut off allows a higher flow rate through the membrane, but might result in larger losses and/or less pure products. The type of solid-liquid separation used and the efficiency of said solid-liquid separation can influence, among other factors, the amount of salts, carbohydrate, amino acids, and protein in the recovered soluble fraction in step b) of the process of the invention.

In an embodiment, the process or the invention comprises, after step b)

converting the RNA into 5'-ribonucleotides.

5'-Phosphodiesterase (5'-Fdase) is preferably used to convert RNA into 5'-ribonucleotides. 5'-Phosphodiesterase can be obtained from a microbial or a vegetable source (for example a malt root extract). An example of a commercially available microbial 5'-Fdase is Enzyme RP-1 produced by Amano (Japan).

Optionally, 5'-AMP is converted to 5'-IMP by a deaminase, for example adenyl deaminase. An example of a commercially available deaminase is Deaminase 500 produced by Amano (Japan).

Treatment of RNA by 5'-Fdase and deaminase can be performed in a two-step or in a single step process.

In another preferred embodiment, the process of the invention comprises after step c):

separating the 5'-ribonucleotides from other soluble material, preferably by centrifugation or filtration. This allows to obtain a yeast extract having a very low turbidity as well as a high amount of 5'-ribonucleotides, e.g. up to 90% w/w, 95% w/w, or even 98% w/w or 99% w/w, all based on total dry matter.

The process of the invention has several benefits. It allows for the production of yeasts extract having a low turbidity and because it may comprise only 2 steps, it is very simple. It may also allow for the production of a cell wall fraction rich in RNA, which can subsequently be converted to 5'-ribonucleotides, and which 5'-ribonucleotides may be purified form the cell wall fraction resulting in a very pure 5'-ribonucleotides fraction. In this way, both a very clear yeast extract may be produced in addition to a cell wall fraction rich in RNA and/or a cell wall fraction rich in 5'-ribonucleotides and/or a very pure 5'-ribonucleotide containing fraction.

In a second aspect, the invention provides a yeast extract characterized in that the turbidity of the yeast extract measured at a dry matter content of 5% is less than 30 NTU. Preferably, the yeast extract is obtainable by the process of the invention.

The invention will now be illustrated by some examples which however do not intend to be limiting.

EXAMPLE 1

Preparation of a Yeast Extract with Low Turbidity

Two litres of cream yeast from *Saccharomyces cerevisiae* were heated to 60° C. Subsequently 0.5 ml Alcalase (commercially available serine protease from Novozymes, Denmark) was added and the mixture was incubated for 4 hours at pH 6.0 and 60° C. The conditions were adjusted to pH 5.1 and 51.5° C. and an additional 2 ml of Alcalase was added to the reaction mixture. The mixture was incubated for 20 hours at pH 5.1, 51.5° C. Next, the mixture or autolysate was heated for 1 hour at 65° C. to inactivate all enzyme activity.

The RNA content of the autolysate was 8.7% w/w based on total dry matter. One part of the autolysate was treated with 5'-phosphodiesterase which resulted in an amount of 5'-GMP of 2.65% w/w, expressed as disodium heptahydrate and based on sodium chloride free dry matter. It follows that the fraction of RNA which was degradable into 5'-ribonucleotides was 83% (w/w).

The other part of the autolysate was subjected to a first solid/liquid separation by way of centrifugation at a pH of either 5.1 (comparative experiment), 4.2 (experiment 1), or 3.5 (experiment 2). The cell wall fractions were collected without further pH adjustment and washed two times with water and analyzed for RNA content. The clear extract (as the supernatant) was adjusted to a dry matter content of either 13% or 2.5% by adding water and was subsequently analyzed for turbidity.

The cell wall fractions were further treated 5'-phosphodiesterase at a temperature of 65° C. and a pH of 5.3. Next, 5'-AMP was converted by the enzyme deaminase into 5'-IMP at a temperature of 55° C. and at pH 5.1. After both the 5'-phosphodiesterase and the deaminase treatment the cell wall fraction was subjected to a second solid/liquid separation by means of centrifugation and the clear fraction was analysed for 5'-ribonucleotide content.

Some samples were also incubated with 5'-Fdase in order to establish whether the RNA present in the samples could be converted into 5'-ribonucleotides (i.e. whether the RNA was in a form degradable into 5'-ribonucleotides by e.g. 5'-Fdase) and some of these samples were also treated with deaminase to convert the 5'-AMP into 5'-IMP. The amount of 5'-GMP, 5'-AMP and 5'-IMP in the samples (expressed as weight percentage of the disodium heptahydrate thereof based on sodium chloride free dry matter) were subsequently determined by means of HPLC according to the following method. 5'-GMP, 5'-AMP and 5'-IMP in yeast extracts were quantified by HPLC using a Whatman Partisil 10-SAX column, a phosphate buffer pH 3.35 as eluent and UV detection. Concentrations were calculated on basis of 5'-GMP, 5'-IMP and 5'-AMP standards. Sodium chloride was determined by measuring the chloride ions in the sample with a Jenway chloride meter PCLM 3 (Jenway, Essex, England) and calculating the corresponding amount of sodium chloride.

TABLE 1

Results of Example 1

|  | Comparative Example A | Experiment 1 | Experiment 2 |
|---|---|---|---|
| pH during the first solid/liquid separation | 5.1 | 4.2 | 3.5 |
| RNA content of the cell wall fraction (% w/w based on dry matter) | 15.2 | 16.7 | 19.9 |
| 5'-GMP content (% w/w) after the phosphodiesterase treatment and before the second solid/liquid separation | 5.3 | 5.7 | 6.6 |
| % of the RNA in the cell wall fraction | 55 | 75 | 90 |
| 5'-GMP content in the clear fraction (% w/w) obtained after the second solid/liquid separation (5'-phosphodiesterase treatment only) | 18.6 | 22.4 | 25.5 |
| 5'-GMP content in the clear fraction (% w/w) obtained after the second solid/liquid separation (5'-phosphodiesterase and subsequent deaminase treatment) | 19.6 | 22.7 | 24.9 |
| 5'-IMP content in the clear fraction (% w/w) obtained after the second solid/liquid separation (5'-phosphodiesterase and subsequent deaminase treatment) | 20.2 | 23.1 | 25.3 |
| Turbidity of the clear extract obtained after the first solid/liquid separation (NTU at 13% dry matter) | 298 | 49 | 31 |
| Turbidity of the clear extract obtained after the first solid/liquid separation (NTU at 2.5% dry matter) | 57 | 9.4 | 6.0 |

RNA was analyzed as follows: RNA was hydrolysed during an alkaline treatment. GMP (i.e. 2'-GMP and 3'-GMP derived from the hydrolysis of RNA) was quantified by means of HPLC, using 5'-GMP as a standard, using a Whatman Partisil 10-SAX column, a phosphate buffer at pH 3.35 as eluent and UV detection. The weight percentage of RNA content based on sodium chloride free dry matter corresponds to ~4 times the weight percentage of free GMP based on sodium chloride free dry matter.
Turbidity was determined by nephelometry with a HACH 2100 N turbidity meter (Hach-Lange, Düsseldorf, Germany) equipped with a tungsten lamp (400-600 nm) at a temperature of 20° C.

EXAMPLE 2

RNA-Partitioning over Cell Walls and Supernatant as a Function of pH

The experiments of Example 1 were repeated at pH values ranging from 2.0 to 5.01. All conditions were identical except that the clear extract (the supernatant) was adjusted to a dry matter content of 5% by adding water before being analyzed for turbidity. Also, RNA in the cell wall fractions was not digested by 5'-Fdase.

TABLE 2

| Results of Example 2 | | | | | | | | |
|---|---|---|---|---|---|---|---|---|
| | Experiment 3 | Experiment 4 | Experiment 5 | Experiment 6 | Experiment 7 | Experiment 8 | Experiment 9 | Experiment 10 |
| pH during the first solid/liquid separation | 2.01 | 2.49 | 2.90 | 3.29 | 3.49 | 3.99 | 4.50 | 5.01 |
| % of the RNA in the cell wall fraction* | 94.6 | 94.7 | 94.1 | 89.4 | 79.8 | 59.5 | 55.3 | 53.8 |
| % of the RNA in the supernatant* | 5.4 | 5.3 | 5.9 | 10.6 | 20.2 | 40.5 | 44.7 | 46.2 |
| Turbidity of the supernatant (NTU at 5% dry matter) | 6.0 | 5.3 | 6.1 | 3.8 | 6.0 | 19.2 | 34.8 | 32.9 |

*the sum of the RNA in the cell walls and the supernatant is 100% by definition

The invention claimed is:

1. A process for producing a yeast extract having a low turbidity comprising:
   a) subjecting a yeast to autolysis; and
   b) subjecting the autolysate to solid/liquid separation and recovering a soluble fraction,
wherein the autolysis in a) is performed at a pH of greater than 5.0, wherein the solid/liquid separation in b) is done at a pH of lower than 4.0 and higher than 1.0 and wherein the turbidity of the yeast extract produced by the process measured at a dry matter content of 5% is less than 20 NTU.

2. The process according to claim 1, wherein the pH in b) is 3.5 or less and higher than 1.0.

3. The process according to claim 1, wherein the pH is higher than 2.0.

4. The process according to claim 1, wherein recovering in b) is done by centrifugation.

5. The process according to claim 1, comprising after b):
   c) converting RNA into 5'-ribonucleotides.

6. The process according to claim 5, comprising after c):
   d) separating the 5'-ribonucleotides from other soluble material.

7. A yeast extract wherein turbidity of the yeast extract measured at a dry matter content of 5% is less than 20 NTU.

8. The yeast extract obtainable by the process of claim 1.

* * * * *